United States Patent [19]

Isono et al.

[11] Patent Number: 5,156,955
[45] Date of Patent: Oct. 20, 1992

[54] NUCLEOSIDE OXIDASE AND ASSAY METHOD UTILIZING SAME

[75] Inventors: Yoshikazu Isono, Otsu; Masami Hoshino, Kusatsu, both of Japan

[73] Assignee: Otsuka Foods Co., Ltd., Osaka, Japan

[21] Appl. No.: 425,217

[22] PCT Filed: Feb. 1, 1989

[86] PCT No.: PCT/JP89/00105
§ 371 Date: Oct. 4, 1989
§ 102(e) Date: Oct. 4, 1989

[87] PCT Pub. No.: WO89/07137
PCT Pub. Date: Aug. 10, 1989

[30] Foreign Application Priority Data
Feb. 4, 1988 [JP] Japan .................. 63-25462
Aug. 5, 1988 [JP] Japan .................. 63-196632

[51] Int. Cl.$^5$ .................. C12A 1/26; C12A 1/32; C12P 1/00; C12N 1/20
[52] U.S. Cl. .................. 435/25; 435/26; 435/28; 435/41; 435/136; 435/253.4; 435/874; 435/15; 435/18; 435/4
[58] Field of Search .................. 435/25, 190, 252.34, 435/874, 92, 194, 196, 850

[56] References Cited

U.S. PATENT DOCUMENTS 3,150,058  9/1964  Katagiri et al. .................. 435/92
4,385,112  5/1983  Misaki et al. .................. 435/6

OTHER PUBLICATIONS

Swings et al., Intl. J. Sys. Bact. 33(2):409 (1983).
Isono et al., Agric. Biol. Chem. 52(8) 2135 (1988).
Hoshino et al., Agri. Biol. Chem. 53(2) 399 (1989).
Isono et al., Agr. Biol. Chem. 53(8) 2197 (1989).
ATCC Cataloge 7th Ed. Gherna & Pienta (1989).
Bergey's (1984) Systematic Bacteriology V-1 Section 4, Gram-Negative Aerobic Rods and Cocci 140-213.

Primary Examiner—Robert A. Wax
Assistant Examiner—Miguel Escallon
Attorney, Agent, or Firm—Sughrue, Mion, Zinn, Macpeak & Seas

[57] ABSTRACT

The present invention provides a novel nucleoside oxidase YT-1 serving as an enzyme for catalyzing oxidation reaction of a nucleoside, and oxidase being characterized in that the oxidase causes the nucleoside to react with molecular oxygen to produce a nucleoside-5'-carboxylic acid via a nucleoside-5'-aldehyde without producing hydrogen peroxide, a process for producing the enzyme, a novel microorganism having ability to produce the enzyme, and a novel analysis or assay method for nucleosides and the like utilizing the enzyme.

7 Claims, 8 Drawing Sheets

NUCLEOSIDE OXIDASE AND ASSAY METHOD UTILIZING SAME

TECHNICAL FIELD

The present invention relates to a novel enzyme for catalyzing the oxidation reaction of nucleosides, and more particularly to a novel nucleoside oxidase YT-1 for causing a neucleoside to react with molecular oxygen to form a nucleoside-5'-carboxylic acid via a nucleoside 5'-aldehyde without forming hydrogen peroxide as a by-product, a process for producing the enzyme, a novel microorganism capable of producing the enzyme, and a novel assay method utilizing the enzyme.

BACKGROUND ART

Known enzymes active on nucleosides include those effecting hydrolysis or deamination thereof, and enzymes (nucleoside oxidases) for catalyzing the oxidation reaction thereof represented by the following equations.

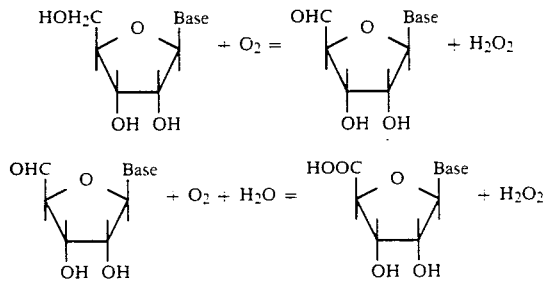

Nucleoside oxidase is usually isolated from microorganisms typical of which is, for example, *Pseudomonas putida*, and the oxidase as purified is used for preparing nucleoside-5'-carboxylic acids, quantitative determination of nucleosides and systems for determining the activity of enzymes or the like wherein a nucleoside is produced or the amount thereof descreases due to a reaction.

However, in the oxidation reaction system wherein the oxidase is used, $H_2O_2$ is inevitably produced, so that in producing the nucleoside-5'-carboxylic acid, the resulting $H_2O_2$ needs to be decomposed by adding catalase to the reaction system. Further when the amount of $H_2O_2$ produced in the reaction system is measured to quantitatively determine the nucleoside, the method has the disadvantage that peroxidase must be used. The method further has the disadvantage, for example, of necessitating a complex determination system (see, for example, Unexamined Japanese Patent Publications SHO 57-58883, SHO 57-68794 and SHO 57-94300).

We have conducted extensive research on nucleoside oxidases derived, for example, from microorganisms and found that a strain belonging to the genus Pseudomonas and newly isolated from soil has ability to produce an enzyme which catalyzes an oxidation reaction different from those involving the activity of the conventional nucleoside oxidases. We have also succeeded in isolating and purifying the enzyme, clarifying the characteristics thereof and developing novel assay or determination techniques utilizing the enzyme. Thus, the present invention has been accomplished.

DISCLOSURE OF THE INVENTION

The present invention provides an enzyme for catalyzing oxidation reaction of a nucleoside, i.e., a novel nucleoside oxidase YT-1 characterized in that the oxidase causes the nucleoside to react with molecular oxygen to produce a nucleoside-5'-carboxylic acid via a nucleoside-5'-aldehyde without producing hydrogen peroxide, a process for producing the enzyme, a novel microorganism having ability to produce the enzyme, and a method of assaying a system containing or for producing a nucleoside by causing the nucleoside oxidase YT-1 to act on a mixture of the system and a chromogenic reagent forming a color on oxidation and measuring the degree of color formation by the chromogenic reagent which is proportional to the quantity of nucleoside in the system.

The nucleoside oxidation reaction catalyzed by the enzyme of the invention is represented by the equations (1) and (2) given below and distinctly differs from the known oxidation reactions effected by nucleoside oxidases. Of course, no nucleoside oxidase is known which catalyzes the reaction represented by the equations (1) and (2).

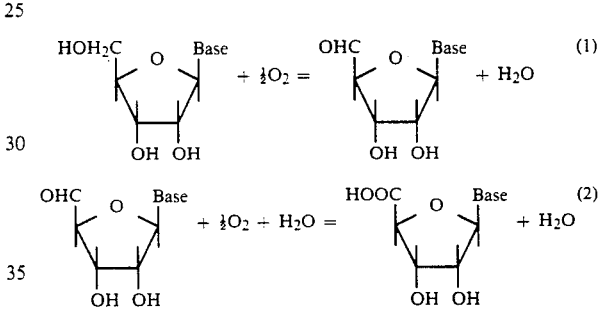

Furthermore, the nucleoside oxidase YT-1 of the present invention effects the nucleoside oxidation reaction of the above equations and, at the same time, exhibits laccase-like activity in accordance with the amount of nucleoside as the unique characteristics of the enzyme. The present enzyme is entirely different from the conventional nucleoside oxidases also in this feature. With the assay method of the invention, the degree of color formation is measured, for example, in terms of absorbance utilizing the laccase-like activity which is unique to the enzyme. Such assay can not be practiced with use of the conventional nucleoside oxidase.

The process of the invention for producing the enzyme of the invention, the characteristics thereof and the present assay method utilizing the same will be described below.

The enzyme of the invention can be produced using strains belonging to the genus Pseudomonas and capable of producing the enzyme. The enzyme producing strain is, for example, a strain newly isolated by the present inventors and having the following characteristics.

I. Mycological Characteristics (A) Morpholocal Characteristics
  (1) The cells are in the form of rods, $0.5 \times 1.5$–$1.7$ μm in size.
  (2) Motile with polar flagellae.
  (3) No spore formation.
  (4) Negative in Gram staining.
(B) Incubation findings (1) Nutrient agar plate Medium growth with circular colonies having a smooth yellow surface.

(2) Nutrient agar slant

Medium growth with a smooth yellow surface.

(3) Nutrient broth culture

Medium growth on the surface of medium.

(4) Gelatin stab culture

Growth on the surface, liquefies gelatin (stratiform).

(C) Physiological Characteristics

| (1) Reduction of nitrate | negative |
| (2) Denitrification | negative |
| (3) Production of indole | negative |
| (4) Production of hydrogen sulfate | negative |
| (5) Hydrolysis of starch | negative |
| (6) Utilization of nitrate | negative |
| (7) Utilization of ammonium salt | positive |
| (8) Pigmentations | |

Produces none of flurescent pigment, pyocyanine and xanthomonadines. Likely to produce a diffusible brown pigment on nutrient agar medium.

| (9) Urease | negative |
| (10) Oxidase | negative to weakly positive |
| (11) Catalase | positive |
| (12) Growth range | |

No growth at pH 4.5. No growth at 4° C. or 41° C. The growth pH is suitably in the range of 5 to 8. The optimum temperature is 35° C.

| (13) Behavior to oxygen | aerobic |
| (14) O—F test (Hugh Leifson method) | oxidative |
| (15) Acid formation from sugars | |
|    D-glucose | positve |
|    D-fructose | positive |
|    D-maltose | positive |
|    D-galactose | positive |
|    D-xylose | positive |
|    D-mannitol | negative |
|    Sucrose | negative |
|    Lactose | positive |
| (16) Decomposition of esculin | positive |
| (17) Arginine dihydrase | negative |
| (18) Lysine decarboxylase | positive |
| (19) Ornithine decarboxylase | negative |
| (20) Phenylalanine deaminase | negative |
| (21) Egg yolk reaction | negative |
| (22) Decomposition of tween 20 | positive |
| (23) Decomposition of tween 80 | positive |
| (24) Accumulation of a poly-$\beta$-hydroxybutyrate | negative |
| (25) Growth factors required | |
|    Requires methionine or cystine. | |

In view of the foregoing characteristics, the present strain was taxonomically investigated with reference to Bergery's Manual of Systematic Bacteriology (1984) and found to belong to the genus Pseudomonas because the present strain (1) is a Gram-negative rod and does not form spores, (2) is catalase-positive, (3) is motile with polar flagellae, (4) decomposes glucose through oxidation, and (5) grows briskly on common agar media at a pH of 7.0. Furthermore, the strain was found identical with *Pseudomonas maltophilia* in such characteristics that the strain (1) requires cystine or methionine for growth, (2) is arginine dihydrolase-negative, (3) does not accumulate poly-$\beta$-hydroxybutyrate, (4) form yellow colonies, (5) does not produce xanthomonadines and (6) has a weak or negative oxidase reaction.

The foregoing results have led us to identify the present strain as a strain of *Pseudomonas maltophilia*. We named the strain *Pseudomonas maltophilia* LB-86. The strain has been deposited with this designation and deposition number FERM BP-2252 in the Fermentation Research Institute, Agency of Industrial Science and Technology, MITI.

The nucleoside oxidase YT-1 of the present invention can be produced by incubating the microorganisms including the strain LB-86 and variants thereof, belonging to the genus Pseudomonas and having ability to produce the nucleoside oxidase YT-1.

These microorganisms can be incubated in a suitable nutrient-containing medium, which can be any of the synthetic media, semisynthetic media and natural media generally used for incubating microorganisms of the genus Pseudomonas and containing carbon sources, nitrogen sources, inorganic substances, etc. Examples of useful carbon sources are carbon compounds which can be assimilated by the microorganism, such as higher fatty acid, starch decomposition product (dextrin), maltose, lactose, glucose, molasses and fructose. These carbon compounds can be used singly, or at least two of them are usable in combination. Examples of useful nitrogen sources are peptone, meat extract, yeast extract, soybean flour, cotton seed flour corn steep liquor and the like. Examples of useful inorganic substances are common salt, and phosphates, sulfates and like inorganic salts of potassium, sodium, magnesium, calcium, zinc, iron and like inorganic metals. Such inorganic substances can be used suitably when required.

The microorganism can be incubated in a liquid or solid. It is usually desirable to conduct the incubation aerobically with stirring for aeration. The incubating conditions, such as the pH of the medium, incubating temperature and incubating time, are selected from among those which are suitble for the growth of the microorganism to be cultured and which will give the desired enzyme in the highest possible yield. For example, it is suitable that the pH of the medium be in the range of about 6 to about 8, and that the incubating temperature be in the range of about 20° to about 35° C. The incubating time to be determined is such that it will result in the greatest accumulation of the desired enzyme produced. Usually, it is in the range of about 12 to about 48 hours. These incubating conditions and method can of course be altered suitably in accordance with the microorganism to be used and the external conditions for incubation.

The culture thus obtained contains the desired enzyme usually as accumulated in its cell fraction. The enzyme can be collected and purified by various methods which are conventionally employed in processes for producing enzymes or the like utilizing microorganisms. Examples of useful purifying means includes means wherein solvent solubility is utilized, means wherein a difference in ion coupling force is utilized, means wherein a difference in molecular weight is utilized, means utilizing a difference in isoelectric point, means utilizing a difference in hydrophobicity, etc. These means can be employed singly or in a suitable combination.

The desired enzyme is collected from the cell fraction by the method to be described below in detail. For example, wet cells are collected by centrifuging or like usual method and then subspended in a phosphate buffer, Tris buffer or the like. The suspension is treated by a suitable combination of cell treating methods such as sonication, French press treatment and lysozyme treatment to obtain a liquid containing crude enzyme.

The crude enzyme-containing liquid is purified by a usual method to obtain a purified enzyme product. First, a precipitate is collected from the liquid, for example, by fractional precipitaion using ethanol, acetone or like organic solvent, or by salting out with use of ammonium sulfate, aluminum sulfate or the like. The precipitate is then chromatographically treated using ion exchange means such as diethylaminoethyldextran, or gel filtration agent such as polyacrylamide gel. The purified enzyme product can further be treated as by lyophilization to obtain a purified powder.

The enzyme of the present invention thus obtained is characterized in that it has enzymatic activity to catalyze the oxidation reaction represented by the foregoing equations (1) and (2), and is also characterized in that it has the following physicochemical properties.

(1) Substrate Specificity

Active on inosine and various other nucleosides but not active on bases such as hypoxanthine, nucleotides such as inosinic acid, ribose, etc.

(2) Temperature and pH Stabilities

Remains in an activity of at least 95% when treated at pH 6.0, 60° C. for 15 minutes, and becomes inactivated when treated at 70° C. for 15 minutes. At least 95% activity remains at pH 5.0 to 6.0 when treated at 37° C. for 60 minutes.

(3) Optimum pH pH 5.0–6.0.

(4) Molecular Weight

About 130,000 as determined by gel filtration.

(5) Isoelectric Point pH 5.3.

(6) Effects of Inhibitors

Inhibited by potassium cianate and sodium azide.

(7) Absorption in Visible Region

No absorption maximum beyond 450 nm in a neutral buffer such as phosphate buffer. Oxidized enzyme not reduced with substrate, sodium hydrosulfite or the like exhibits no absorption maximum beyond 450 nm.

(8) Metal Content

Contains iron.

These physicochemical properties and other properties will be described in examples to follow.

The enzyme of the invention, nucleoside oxidase YT-1, having the foregoing properties can be utilized for the quantitative determination of nucleosides like conventional nucleoside oxidases. More specifically stated, the present enzyme oxidizes nucleosides with molecular oxygen serving as an electron acceptor and is therefore usable for the quantitative determination of the nucleoside by measuring the amount of oxygen consumption. Thus, the present enzyme is usable for assaying of the enzymes whose substrates or reaction products contain nucleosides. For example, the enzyme is usable for measurement of 5'-nucleotidase activity. Furthermore, the enzyme is usable for measuring the fish freshness by measuring the amount of nucleoside in an extract of the fish muscle. The present enzyme is also useful, for example, for producing nucleoside-5'-carboxylic acids.

Especially, the enzyme of the invention has the unique property that when effecting the oxidation reaction of a nucleoside, the enzyme effects a laccase-like reaction in corresponding relation to the amount of nucleoside present. Moreover, the activity to effect the laccase-like reaction is completely in proportion to the amount of nucleoside. Accordingly, this property can be utilized for oxidizing typical laccase substrates such as hydro quinone and also for coupling 4-aminoantipyrine with phenol or an aniline-type compounds or the like to produce quinoneimine, as with laccase from *Polyporous versicolor*. The amount of nucleoside can be quantitatively determined by measuring the amount of pigment thus produced. Additionally, the initial velocity of an enzymatic reaction for releasing a nucleoside can be measured spectroscopically accurately and easily using the enzyme of the invention.

The present invention also provides a novel method of assaying liquid specimens utilizing the unique laccase-like activity of the present enzyme.

The assay method will be described in detail. This method is used for a system containing or for producing a nucleoside and is practiced by causing the nucleoside oxidase YT-1 to act on a mixture of the system and a chromogenic reagent for forming a color on oxidation and measuring the degree of color formation by the chromogenic reagent which degree is proportional to the quantity of nucleoside in the system.

The liquid specimen to be assayed by this method can be any system containing a nucleoside or for producing a free nucleoside (nucleoside producing or releasing enzyme reaction system). Typical examples of such specimens are given below.

(1) Enzymatic activity measuring liquid specimen wherein 5'-nucleotidase is reacted with 5'-inosine monophosphate (IMP), 5'-adenosine monophosphate (AMP) or like 5'-nucleotide to release the inosine, adenosine or like nucleoside.

(2) Enzymatic activity measuring liquid specimen wherein 3'-nucleotidase is reacted with 3'-IMP, 3'-AMP or like 3'-nucleotide to release the inosine, adenosine or like nucleoside.

(3) Liquid specimen for measuring the freshness of fish, meat of beast or the like wherein a component of the living body is decomposed to produce nucleosides or which contains such nucleosides.

(4) Liquid specimen for measuring the activity of ribonuclease or deoxyribonuclease wherein the ribonuclease or deoxyribonuclease is reacted with RNA, DNA oligo-nucleotide or the like, and alkali phosphatase or the like is further reacted with the resulting nucleotide to release nucleoside.

(5) Reagent liquid specimens for nucleosides such as adenosine, deoxyuridine, xanthosine, thymidine, uridine, guanosine, cytidine, deoxyinosine and the like.

(6) Liquid specimens for measuring the activity of enzymes, such as inosinase, for hydrolyzing nucleosides as substrates.

Of these specimens, examplary of the enzymatic activity measuring specimen (1), i.e. nucleoside releasing enzyme reaction system, is a system containing human serum and a nucleotide. When the assay method of the invention is practiced for the system, the activity of 5'-nucleotidase in the human serum is measured. This method is very useful for testing the liver function. The conventional methods for measuring the activity of 5'-nucleotidase in the human serum include a method wherein 5'-AMP is used as a substrate to determine the resulting free inorganic phosphor, and an enzymatic method utilizing adenosine deaminase or glutamic acid dehydrogenase, whereas the method wherein inorganic phosphor is determined requires a prolonged reaction time, complex procedure and compensastion of the activity of alkali phosphatase conjointly present. The enzymatic method has the drawbacks of necessitating a complex measuring system and preliminary reaction for about 30 minutes prior to the start of the reaction. In contrast, the present assay method can be practiced by a very simple procedure with a higher sensitivity than heretofore possible usually within a very short period of time, i.e., about 2 to about 5 minutes, to measure the contemplated activity of 5'-nucleotidase in the human serum.

The chromogenic reagents which form a color on oxidation include reagents which are each in the form of a single compound and exhibit absorption in the visible region on oxidation, and those which are each in the form of a combination of at least two compounds and exhibit absorption in the visible region on oxidation. Examples of useful single compounds are various laccase substrates such as o-tolidine, o-toluidine, o-dianisidine, 10-N-methylcarbamoyl-3,7-dimethylamino-10-H-phenothiazine, bis [3-bis(4-chlorophenyl)-methyl-4-dimethylaminophenyl] amine and like aniline-type substances, etc. Exemplary of the combination of at least two compounds is the combination of a so-called coupler and a Trinder's reagent (hydrogen donator), such as 4-aminoantipyrine and phenol, as generally used conventionally as a clinical diagnosing chemical. Examples of useful couplers are, besides 4-aminoantipyrine (4-AA), 2,6-dibromoaminophenol, 3-methylbenzothiazolinone-hydrazone, etc. Examples of useful Trinder's reagents (hydrogen donators) are, besides phenol, β-chlorophenol, 2,4-dichlorophenol, 2,6-dichlorophenol, N,N-dimethylaniline (DMA), N-ethyl-N-(2-hydroxy-3-sulfopropyl)-m-anisidine (ADOS), N-ethyl-N-(2-hydroxy-3-sulfopropyl)-aniline (ALOS), N-ethyl-N-(2 -hydroxy-3-sulfopropyl)-m-toluidine (TOOS), N-ethyl-N-sulfopropyl)-m-anisidine (ADPS), N-ethyl-N-sulfopropylaniline (ALPS), N-ethyl-N-sulfopropyl-3,5-dimethoxyaniline-sodium salt (DAPS), N-ethyl-N-(2-hydroxy -3-sulfopropyl)-3,5-dimethoxyaniline-sodium salt (DAOS), N-sulfopropyl-3,5-dimethoxyaniline (HDAPS), N-(2-hydroxy-3-sulfopropyl)-3,5-dimethoxyaniline (HDAOS), N-ethyl-N-(2-hydroxy-3-sulfopropyl)-3,5-dimethylaniline (MAOS), N-ethyl-N-sulfopropyl-3,5-dimethylaniline (MAPS), N-ethyl-N-sulfopropyl-m-toluidine (TOPS), $N^2$-ethyl-$N^2$-(3-methylphenyl)-N'-acetylethylenediamine (EMAE) and the like.

To practice the assay method of the invention, the enzyme of the invention is caused to act on the mixture of specimen and chromogenic reagent. This can be done usually by adding the chromogenic reagent to the specimen and further adding the present enzyme thereto, or adding the present enzyme to the chromogenic reagent and further adding the specimen thereto, and thereafter allowing the resulting mixture to stand at a specified temperature for a predetermined period of time. The reagent then forms a color due to an enzymatic reaction. In the above method, the specimen is usable as suitably diluted. Examples of useful diluents are various buffers such as phosphate buffer and Tris buffer, water, etc. The amount of reagent to be used in the enzyme reaction system is not limited specifically but is determined suitably. It is usually such that the concentration of the chromogenic reagent in the reaction system is about 0.1 to about 10 mM. It is suitable that the present enzyme be used in an amount of about 0.05 to about 10 units per milliliter of the reaction system, and that the specimen be used in such an amount that the concentration of the nucleoside in the specimen is in the range of about 0 to not higher than about 0.2 mM in the reaction system. Although the reaction conditions for the enzyme reaction system are not limited specifically, the temperature is usually about 20° to about 40° C. to be suitable. The reaction time can be determined suitably in accordance with the amount of the present enzyme, reaction temperature, pH, etc. and is generally very short. The reaction is completed within about 20 minutes. The pH of the reaction system is usually in the range of about 3 to about 10, and the reaction proceeds satisfactorily in this range. Generally, the pH is suitably in the range of about 4 to about 8.

With the method of the invention, the degree of color formation effected in the enzyme reaction mixture is measured to determine the resulting variation in the amount of nucleoside in the specimen. The degree of color formation can be measured in the usual method by specroscopically measuring the absorption in the visible region of the pigment or like substance produced by the enzyme reaction and exihibiting absorption in the visible region. For example, with a system wherein 4-amino-antipyrine and phenol produce quinoneimine pigment, the degree of color formation can be determined by measuring the absorbance at 500 nm with a spectrophotometer. Typical examples of other systems and absorbance measuring procedures in these systems will be described in detail in examples to follow.

In the case where the specimen to be assayed by the above method of the invention is an enzyme reaction system wherein a nucleoside is to be released, e.g., a liquid containing nucleotidase or the like, the reaction to be effected by the present enzyme is conducted in the cell of the spectrophotometer to determine the resulting increase in absorbance per unit time, whereby the enzymatic activity of the nucleotidase or the like can be measured.

Thus, the present invention provides a novel assay method which utilizes the enzyme of the invention and which is very useful for the quantitative determination of necleosides and also for measurig the activity of enzymes in systems for producing or releasing nucleosides.

EXAMPLES

The present invention will be described in greater detail with reference to the following examples. The activity of the nucleoside oxidase was measured by the following method.

Method of Measuring Nucleoside Oxidase Activity

A 1 ml quantity of 100 mM phosphate buffer (pH 6.0) containing 7 mM inosine is placed into the cell of an enzyme electrode, 5 μl of enzyme sample is further placed in, and the initial rate of oxygen consumption is measured at 25° C. by measuring with time the decrease in the amount of dissolved oxygen which is about 250 μM in saturated state at 25° C., using the enzyme electrode. The consumption of 1 μM of oxygen per minute is taken as 1 unit (U).

The drawings referred to in examples show the following.

EXAMPLE 1

Figure 1:
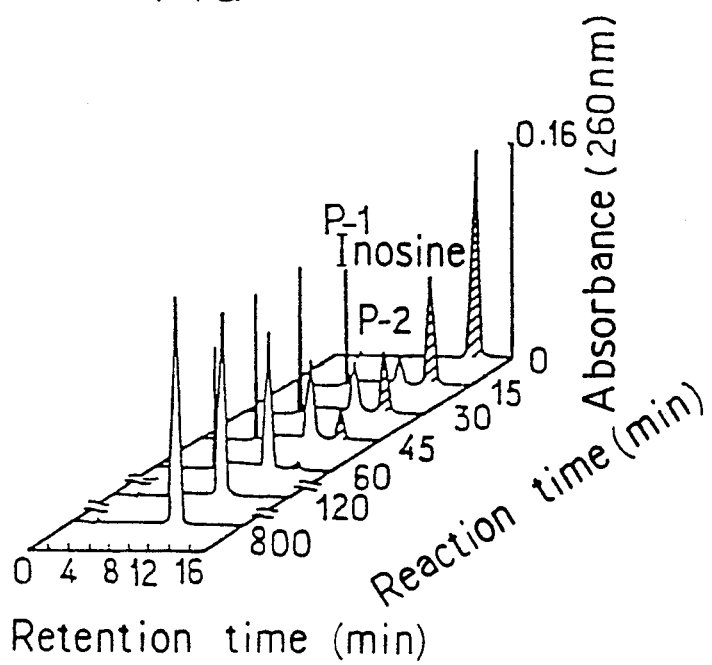
FIG. 1 is a diagram showing the result of high performance liquid chromatography conducted for the reaction product obtained by oxidizing inosine as a substrate using the present enzyme, the result being obtained by enzymatic activity test I according to the invention.

A 100 ml quantity of bouillon medium (1% meat extract, 1% peptone and 0.5% NaCl, the same as hereinafter) as placed in a 500-ml Sakaguchi flask was inoculated with Pseudomonas maltophilia LB-86, FERM BP-2252), followed by incubation with shaking (110 r.p.m.) at 25° C. for 12 hours to obtain a culture.

Six liters of sterilized bouillon medium containing 0.07% of defoaming agent "Adekanol" (product of Asahi Denka Kogyo Co., Ltd.) added thereto and placed in a 10-liter jar fermenter was inoculated with the resulting culture in an amount of 2%. The culture was incubated at a temperature of 25° C. for 12 hours with shaking at 250 r.p.m. and with aeration at a rate of 6 liters/min. After the completion of incubation, the cells were collected, suspended in 1 liter of phosphate buffer (pH 6.0) and sonicated for 15 minutes under the conditions of 20 kHz and 200 W, whereby a cell extract was obtained.

The extract was 1.2 U/ml in nucleoside oxidase activity.

EXAMPLE 2

A 100 ml quantity of bouillon medium placed in a 500-ml Sakaguchi flask was inoculated with Pseudomonas maltophilia LB-86, followed by incubation with shaking (110 r.p.m.) at 25° C. for 12 hours to obtain a culture.

A 100 ml of sterilized yeast extract-glucose medium (2.5% yeast extract, 3% glucose, 0.1% KCl, 0.1% $KH_2PO_4$ and 0.05% $MgSO_4 7H_2O$, pH 7.2) placed in a 500-ml Sakaguchi flask was inoculated with the resulting culture in an amount of 2%. The culture was incubated for 24 hours at a temperature of 25° C. with shaking at 110 r.p.m. After the completion of incubation, the cells were collected and suspended in phosphate buffer (pH 7.0) placed in flasks, each containing 30 ml of the buffer. The suspension was thereafter sonicated under the same conditions as in Example 1 to obtain a cell extract.

The extract was 7.0 U/ml in nucleoside oxidase activity.

EXAMPLE 3

To 272 ml of cell extract prepared in the same manner as in Example 2 was added 60 ml of 20% streptomycin sulfate, the resulting precipitate was removed by centrifugation, and ammonium sulfate was added to the supernatant to a concentration of 35%. After removing the resulting precipitate, ammonium sulfate was further added to the supernatant to a concentration of 60%. The resulting mixture was allowed to stand overnight at a low temperature to form a precipitate, which was then collected and dissolved in 20 mM phosphate buffer (pH 6.0). The solution was dialyzed in a dialyzer tube for 1 day. The dialyzate was applied to DEAE- Toyopearl 650M column (product of Tosoh Co.) as equilibrated with 20 mM phosphate buffer (pH 6.0), followed by thorough washing with the same buffer and linear gradient elution with 0 to 0.5M common salt.

The active fraction was concentrated with Amicon membrane (product of Amicon), 20000 in fractionating molecular weight. For gel filtration, the concentrate was applied to Sephacryl S-200 column (product of Pharmacia) equilibrated with 20 mM phosphate buffer (pH 6.0). The active eluate fractions were collected, concentrated again with Amicon membrane, 20000 in fractionating molecular weight and then subjected to gel filtration with Sephacryl S-200.

The active eluate fractions were collected and lyophilized, giving a purified nucleoside oxidase YT-1.

The pure product was found single by disk electrophoresis.

Table 1 shows the result of purification.

TABLE 1

| Purification steps | Yield (ml) | Specific activity (U/mg) | Yield (%) |
| --- | --- | --- | --- |
| Cell extract | 272 | 0.267 | 100 |
| Ammonium sulfate fraction | 38 | 1.06 | 94.8 |
| As dialyzed | 97 | 1.92 | 82.2 |
| DEAE-Toyopearl | 102 | 9.0 | 58.0 |
| Sephacryl S-200 | 23 | 13.4 | 41.1 |
| Sephacryl S-200 | 19 | 15.0 | 34.9 |

The purified sample of nucleoside oxidase YT-1 of the invention obtained in Example 3 was tested for properties as will be described below in detail.

(1) Enzymatic Activity Test I (1) Detection of oxidation reaction product

Ten U of the enzyme sample as dissolved in a suitable amount of water was placed into a dializer tube, which was then placed into 100 ml of 7 mM inosine solution for reaction.

During a reaction period of 0 to 800 minutes, the reaction mixture was partly collected at suitable time intervals and analyzed by high performance liquid chromatography (HPLC) with a column of Fine SIL $C_{18}$ (product of Japan Spectroscopic Co., Ltd.) using as a solvent 50 mM phosphate buffer (pH 3.0)/methanol=95/5 at a flow rate of 1.5 ml/min. Absorption was detected at 260 nm.

FIG. 1 shows the result obtained during the specified period.

With reference to the diagram, the retention time (min) is plotted as x-axis, the reaction time (incubation time, min) as y-axis, and the absorbance at 260 nm as z-axis.

FIG. 1 reveals the following. The amount of inosine decreased with time, and two peaks (P-1 and P-2) appeared. The peak P-1 enlarged in the initial stage of the reaction, then diminished and thereafter disappeared. The peak P-2 only remained eventually.

When the peak P-1 was separated off by HPLC and reacted with the enzyme sample (nucleoside oxidase), it was found that the peak changed into P-2 with consumption of oxygen. On the other hand, P-2, when reacted with the enzyme sample, exhibited no change.

The above result shows that the enzyme sample of the invention acts to oxidize inosine to form P-1 and further oxidizes P-1 into P-2.

(2) Identification of reaction product (2)-1 Preparation of P-1 and P-2

The enzyme sample (100 U) accommodated in a dializer tube was placed into 100 ml of aqueous inosine solution(2 mg/ml), followed by reaction at 37° C. overnight with stirring for aeration to produce P-2. After removing the tube, the reaction mixture was adjusted to a pH of 3.0 with hydrochloric acid, and the resulting crystals of P-2 were collected by centrifugation, washed with a hydrochloric acid solution (pH3.0) and dried in a vacuum, giving about 190 mg of P-2 crystals.

The enzyme sample (10 U) as placed in a dializer tube was reacted with an aqueous solution of inosine in the same manner as for the preparation of P-2. The reaction mixture was collected from time to time and analyzed by HPLC. When the accumulation of P-1 increased (37° C., about 30 minutes), the enzyme-containing tube was removed to terminate the reaction. The reaction mixture was concentrated in a vacuum and subjected to HPLC to separate off a P-1 fraction, which was then purified by lyophilization to obtain P-1 powder.

(2)-2 Identification of base component and sugar of P-1 and P-2

P-1, P-2 and inosine were each hydrolyzed with 1N hydrochloric acid at 100° C. for 1 hour. Each mixture obtained was analyzed to identify the base and sugar contained therein.

Thin-layer chromatography and HPLC revealed that the base component of each test specimen exhibited the same behavior as the standard product of hypoxanthine. Thus, the base components of P-1 and P-2 can be identified as hypoxanthine the same as inosine.

The sugar anlaysis by the thin-layer chromatography detected D-ribose from the decomposition mixture of inosine but revealed a spot at a different position from D-ribose for the decomposition mixtures of P-1 and P-2.

This indicates that P-1 and P-2 contain the sugar portion of inosine as oxidized.

(2)-3 Identification of P-1

P-1 was reduced with 1.2 times the equivalent weight of sodium borohydride. When analyzed by thin-layer chromatography and HPLC, the reduction product agreed with the standard product of inosine in behavior. Accordingly, the product obtained by reducing P-1 with sodium borohydride was identified as inosine. The structure which can be reduced to original inosine as a substrate is inosine-5'-aldehyde only. This was substantiated also by NMR spectrum and IR spectrum. From these results, P-1 was identified as inosine-5'-aldehyde.

(2)-4 Identification of P-2

$C^{13}$-NMR spectrum and $H^1$-NMR spectrum of a sample of P-2 crystal were measured.

Complete coupling and decoupling were resorted to for $C^{13}$-NMR. For $H^1$-NMR, spectrum measurement was done in dimethyl sulfoxide (DMSO-$d_6$) and then in the same with heavy water ($D_2O$) added thereto.

Table 2 shows the signals determined in view of the chemical shift, binding constant, etc. Consequently, P-2 was identified as inosine-5'-carboxylic acid.

TABLE 2

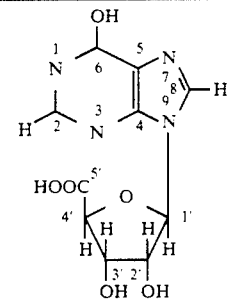

| | Chemical shift (ppm) | Multiplicity | Coupling constant (Hz) |
|---|---|---|---|
| C-2 | 146.22 | d | |
| C-4 | 148.74 | s | |
| C-5 | 124.11 | s | |
| C-6 | 156.65 | s | |
| C-8 | 138.43 | d | |
| C-1' | 87.01 | d | |
| C-2' | 73.39 | d | |
| C-3' | 74.11 | d | |
| C-4' | 82.71 | d | |
| C-5' | 172.08 | s | |
| H-2 | 8.09 | s | |
| H-8 | 8.42 | s | |
| H-1' | 6.02 | d | 6.7 |
| H-2' | 4.47 | dd | (+$D_2O$) 6.7/5.1 |
| H-3' | 4.30 | dd | (+$D_2O$) 5.1/2.3 |
| H-4' | 4.42 | d | 2.3 |
| H-5' | 12.43 | s | |

In the above table, "s" stands for singlet, and "d" for doublet.

(3) Stoichiometry of the reaction

One U of the enzyme sample was added to 1 ml of 100 mM phosphate buffer containing 50 nanomoles of inosine. The amount of oxygen consumption was determined by an oxygen electrode, the amount of P-2 produced from the peak area of HPLC, and the amount of hydrogen peroxide by the phenol-4-aminoantipyrine peroxidase method and the ferrithiocyanide method (Ronald Thurman et al., Eur. J. Biochem., 25, 420–430 (1972)).

Consequently, 47 nanomoles of P-2 was produced from 50 nanomoles of inosine with oxygen consumption of 51 nanomoles. No hydrogen peroxide was detected.

Next, one U of the enzyme sample was added to 1 ml of 100 mM phosphate buffer containing 100 nanomoles of P-1 to similarly determine the amount of oxygen consumption, amount of P-2 produced and amount of hydrogen peroxide.

Consequently, 97 nanomoles of P-2 was produced from 100 nanomoles of P-1 with oxygen consumption of 48 nanomoles. No hydrogen peroxide was detected.

Addition of 1 U of catalase to the above reaction systems resulted in no difference in the amount of oxygen consumption. The nucleoside oxidase sample was found to have neither catalase activity nor peroxidase activity. These results also indicate that the present reaction produces no hydrogen peroxide.

The results given above reveal that the enzyme of the invention oxidizes 1 mole of inosine with ½ mole of oxygen as an electron acceptor to form one mole of inosine-5'-aldehyde and 1 mole of water, and further oxidizes 1 mole of inosine-5'-aldehyde with ½ mole of oxygen as an electron acceptor to form 1 mole of inosine-5'-carboxylic acid.

(2) Enzymatic Activity Test II (1) Identification of reaction product obtained from 1,4-hydroquinone as substrate and stoichiometry One U of the enzyme sample was added to 1 ml of 100 mM phosphate buffer (pH 7.0) containing 0.5 μM of inosine and 0.2 μM of 1,4-hydroquinone to effect reaction at room temperature for 10 minutes. The reaction product was analyzed by HPLC.

Consequently, the position of elution was found to be in agreement with the corresponding position of the standard product of p-quinone.

The reaction product was also found identical with the standard product in UV spectrum.

Thus, the reaction product was identified as p-quinone.

One U of the enzyme sample was added to 1 ml of 100 mM phosphate buffer (pH 7.0) containing 0.06 μM of inosine and 0.12 μM of 1,4-hydroquinone to effect reaction at room temperature for 10 minutes, and the amount of oxygen consumed was measured using an oxygen electrode.

The amount of oxygen consumption was found to be 0.115 μM. It therefore follows that 0.055 μM of oxygen which is 0.115 μM minus 0.06 μM, the amount of oxygen used for oxidizing inosine, was used for oxidizing 0.12 μM of 1,4-hydroquinone.

Thus, the present enzyme oxidizes 1 mole of 1,4-hydroquinone with ½ mole of oxygen to produce 1 mole of p-quinone and 1 mole of water. This reaction is therefore identical with the reaction of laccase (Laccase EC 1.10.3.2) already known.

(2) Relation of nucleoside oxidation with laccase activity

When the present enzyme is mixed with a laccase substrate such as 1,4-hydroquinone, no reaction occurs. However, if inosine, adenosine or like nucleoside is present in this reaction system, the laccase reaction takes place. In other words, the laccase activity of the present enzyme requires presence of the nucleoside. This fact has been substantiated by the following test.

One U of the present enzyme was caused to act on 1 ml of 100 mM phosphate buffer (pH 7.0) containing 0.06 μM of inosine and 0.02, 0.06, 0.12 or 0.6 μM of 1,4-hydroquinone to determine the amount of resulting oxygen consumption and the amount of p-quinone formed. Table 3 shows the result.

TABLE 3

| 1,4-Hydroquinone (μM) | Amount of oxygen consumption (μM) | Amount of p-quinone formed (μM) |
|---|---|---|
| 0.02 | 0.069 | 0.019 |
| 0.06 | 0.089 | 0.060 |
| 0.12 | 0.112 | 0.115 |
| 0.60 | 0.115 | 0.119 |

Table 3 reveals that when oxidizing 1 mole of nucleoside with 1 mole of oxygen as an electron acceptor, the present enzyme effects the laccase reaction with 1 mole of oxygen as an electron acceptor, concurrently with but separately from the nucleoside oxidation.

(3) Activity on phenol and 4-aminoantipyrine

Like the known laccase (as originating from *Polyporus versicolor*), the present enzyme causes phenol and 4-aminoantipyrine to undergo a coupling reaction through oxidation in the presence of a nucleoside to produce red quinoneimine pigment. The red pigment thus produced is found identical with the quinoneimine pigment produced by the conventional oxidation reaction between phenol and 4-aminoantipyrine effected by peroxidase in the presence of hydrogen peroxide, from the UV and visible absorption spectra, HPLC elution position, etc. of the pigment.

Figure 2:
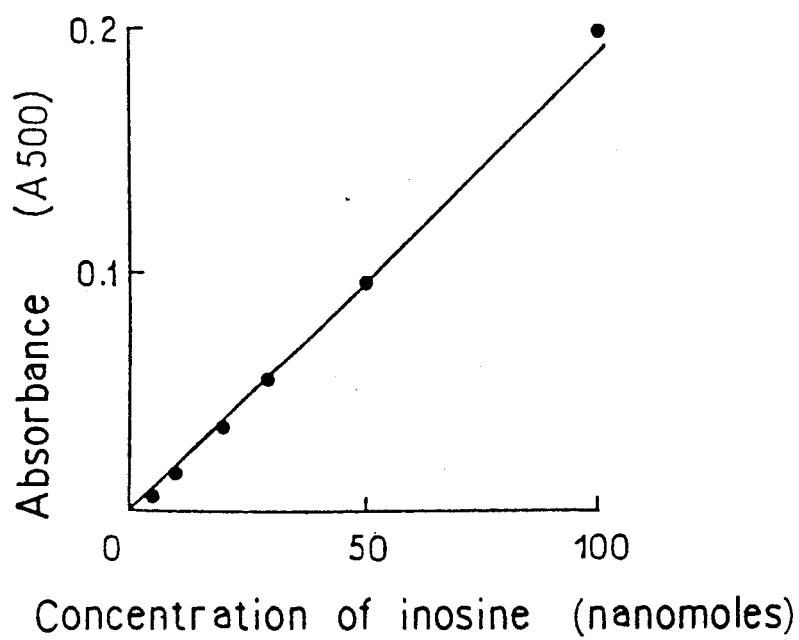
FIG. 2 is a diagram showing the result obtained by enzymatic activity test II according to the invention wherein inosine serving as a substrate was oxidized using the present enzyme in the presence of phenol and 4-aminoantipyrine to produce quinoneimine pigment, the drawing showing the relationship between the degree of color formation by the pigment and the concentration of the substrate.

The present enzyme was tested for the relationship between the preduction of quinoneimine pigment (degree of color formation) and the amount of nucleoside as will be described below. Inosine serving as the nucleoside was added at a specified concentration to 3 ml of 100 mM phosphate buffer (pH 7.0) containing 10 mM phenol and 4-aminoantipyrine, and 1 U of the present enzyme was also added to the buffer to effect reaction and color formation. FIG. 2 shows the result.

With reference to the diagram, the concentration of inosine (in nanomoles) is plotted as abscissa, and the absorbance at 500 nm as ordinate.

FIG. 2 shows that there is a linear relationship between the amount of nucleoside and color formation, consequently indicating that the present enzyme is usable for the colorimetry of nucleosides utilizing the above reaction.

(3) Substrate Specificity Test

Using the compounds listed in Table 4 as substrates, the activity of the present enzyme thereon was determined (relative to the activity thereof on inosine, taken as 100).

TABLE 4

| Substrate | Concentration (mM) | Relative activity (%) |
|---|---|---|
| Neucleoside | | |
| Inosine | 10 | 100 |
| Adenosine | 10 | 97.3 |
| Guanosine | 10 | 121 |
| Xanthosine | 10 | 125 |
| Uridine | 10 | 92.8 |
| Cytidine | 10 | 77.5 |
| Deoxyinosine | 10 | 80.7 |

TABLE 4-continued

| Substrate | Concentration (mM) | Relative activity (%) |
|---|---|---|
| Deoxyadenosine | 10 | 81.4 |
| Deoxyguanosine | 10 | 92.3 |
| Deoxythymidine | 10 | 77.3 |
| Thymidine | 10 | 55.8 |
| Nucleic acid base | | |
| Hypoxanthine | 5.2 | 0 |
| Xanthine | 0.4 | 0 |
| Adenine | 10 | 0 |
| Guanine | 0.4 | 0 |
| Thymine | 20 | 0 |
| Cytosine | 20 | 0 |
| Uracil | 20 | 0 |
| Sugar | | |
| D-ribose | 20 | 0 |
| D-ribose-1-phosphoric acid | 20 | 0 |
| D-ribose-5-phosphoric acid | 20 | 0 |
| 2-Deoxy-D-ribose | 20 | 0 |
| Nucleotide | | |
| 5'-AMP | 10 | 0 |
| 5'-IMP | 10 | 0 |
| 5'-GMP | 10 | 0 |
| 5'-ADP | 10 | 0 |
| 5'-ATP | 10 | 0 |
| 2'(3')-IMP | 10 | 0 |
| 2'(3')-UMP | 10 | 0 |

Table 4 shows that the present enzyme acts on nucleosides but does not act on nucleic acid bases or sugars as present singly, nor does it act on nucleotides.

It is seen that the sugar portion of the nucleoside on which the enzyme acts may be ribose or deoxyribose, and the base portion can be various.

(4) Specificity Test on Laccase Substrate

The present enzyme was tested for the substrate specificity of its laccase-like activity in the presence of 7 mM inosine in the following manner. One unit of the present enzyme was added to a specimen containing 7 mM of inosine and 1 mM of the laccase substrate shown in Table 5, and the mixture was allowed to stand for 5 minutes. The absorption spectrum of the specimen was obtained before and after the addition of the enzyme. Table 5 shows the result.

TABLE 5

| Laccase substrate | Maximum absorption before reaction | Change in absorption spectrum due to reaction |
|---|---|---|
| Hydroquinone | 286 nm | New peak at 243 nm |
| p-Aminophenol | 295 nm | New peak at 360 nm and 460 nm |
| p-Phenylendiamine | 286 nm | New peak at 490 nm |
| Caffeic acid | 284 nm 310 nm | New peak at 310 nm Peak before reaction diminished |
| Pyrogallol | 266 nm | New peak at 370 nm and 420 nm |
| Orcinol | 271 nm | New peak at 340 nm |
| p-Quinone | 243 nm | No change |
| 4-AA + phenol | No absorption in visible region | New peak at 550 nm |
| 4-AA + p-chlorophenol | No absorption in visible region | New peak at 500 nm |
| 4-AA + TOOS | No absorption in visible region | New peak at 500 nm |
| 4-AA + MAOS | No absorption in visible region | New peak at 600 nm |

Table 5 shows that the present enzyme acts on various laccase substrates in the presence of inosine.

We have found that besides inosine, nucleosides, such as those listed in Table 4, which serve as substrates for various nucleoside oxidases are useful for causing the present enzyme to exhibit the laccase-like activity.

(5) Temperature and pH Tests (1) Temperature stability

The present enzyme was treated in 100 ml of phosphate buffer (pH 6.0) for 15 minutes and thereafter checked for remaining activity.

Figure 3:
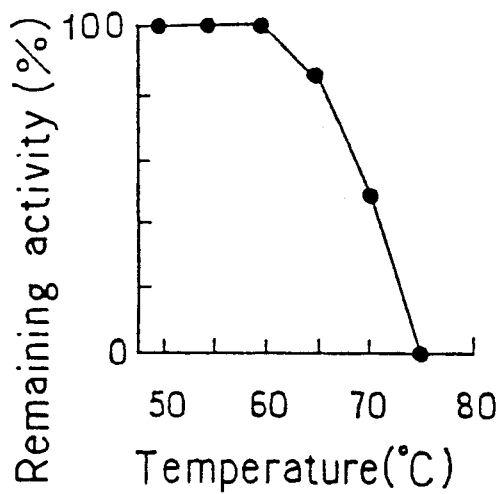
FIG. 3 is a diagram showing the result obtained by checking the present enzyme for temperature stability.

The result is shown in FIG. 3 (abscissa=temperature, ordinate=remaining activity), which reveals that the enzyme remains stable even when treated at 60° C. for 15 minutes.

(2) pH stability

The present enzyme was treated at varying pH values at 37° C. for 60 minutes and thereafter checked for remaining activity at pH 6.0.

Figure 4:
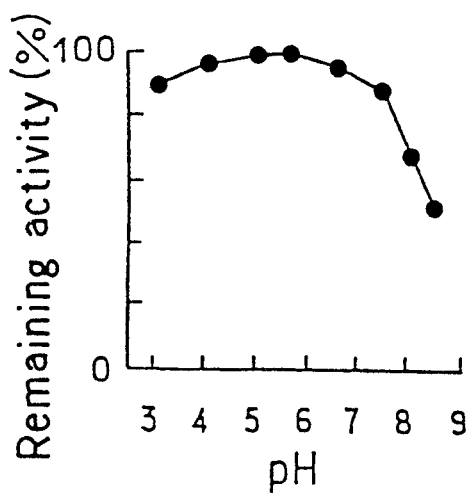
FIG. 4 is a diagram showing the result obtained by checking the present enzyme for pH stability.

The result is given in FIG. 4 (abscissa=pH, ordinate=remaining activity), which shows that the enzyme is stable at a pH of 5 to 6.

(3) Optimum pH

Figure 5:
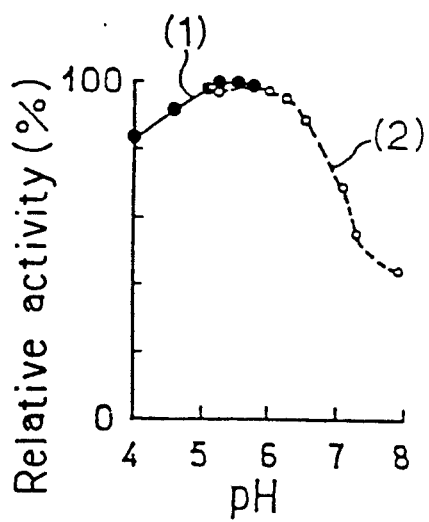
FIG. 5 is a diagram showing the result obtained by checking the present enzyme for optimum pH.

As seen in FIG. 5 (abscissa=pH, ordinate=relative activity), the optimum pH of the present enzyme was found to be 5 to 6. FIG. 5, (1) represents acetate buffer ($\mu$=0.05), and (2) represents phosphate buffer ($\mu$=0.05).

(4) Optmum temperature

The oxygen electrode for use in measuring the activity of the present enzyme is unable to give accurate measurements at temperatures exceeding 40° C. Within the range of up to 40° C., the enzyme exhibited the highest activity at 40° C.

(6) Molecular Weight Measuring Test

The molecular weight of the present enzyme was measured by gel filtration method on a column (2.5 cm in diameter, and 90 cm in length) of Sephacryl S-200 (product of Pharmacia).

The molecular weight thus determined was 130,000.

(7) Isoelectric Point Test

The enzyme was electrophoresced with cooling (4° C.) for 48 hours using Carrier-Ampholite of pH 3.5–10.5 (LKB-Produkter AB. Sweden) and an electrofocusing device produced by LKB to determine the isoelectric point of the enzyme.

The isoelectric point of the present enzyme thus determined was pH 5.3.

(8) Effects of Inhibitors

A solution of the present enzyme (0.02 U) was caused to act on inosine at pH 6.0 and 25° C. for 10 minutes in the presence of various inhibitors, and the enzymatic activity was thereafter measured.

Table 6 shows the result.

TABLE 6

| Inhibitor | Concentration (mM) | Relative activity (%) |
|---|---|---|
| None | — | 100 |
| Potassium cyanate | 1 | 34.8 |
| Potassium cyanate | 10 | 0 |
| Hydroxylamine | 1 | 87.8 |
| Hydroxylamine | 10 | 63.2 |
| Sodium azide | 1 | 81.5 |
| Sodium azide | 10 | 45.6 |
| EDTA | 1 | 101 |

TABLE 6-continued

| Inhibitor | Concentration (mM) | Relative activity (%) |
|---|---|---|
| o-Phenanthroline | 1 | 94.7 |
| α,α'-Dipyridyl | 1 | 96.7 |
| Sodium N,N'-Diethylditio-carbamate | 1 | 271 |
| Quinacrine | 1 | 95.6 |
| Hydrazine sulfate | 1 | 101 |
| Iodoacetic acid | 1 | 100 |
| Mercury p-chorobenzoate | 1 | 98.9 |
| Phenylmethylsulfonyl fluoride | 1 | 95.3 |
| $HgCl_2$ | 1 | 69.2 |
| $Pb(CH_3COO)_2$ | 1 | 81.3 |
| N-Bromosuccinimide | 1 | 0 |

Table 6 shows that the present enzyme is inhibited by potassium cyanate, sodium azide, N-bromosuccinimide, etc.

(9) UV and Visible Absorption Spectral Analysis

Figure 6:
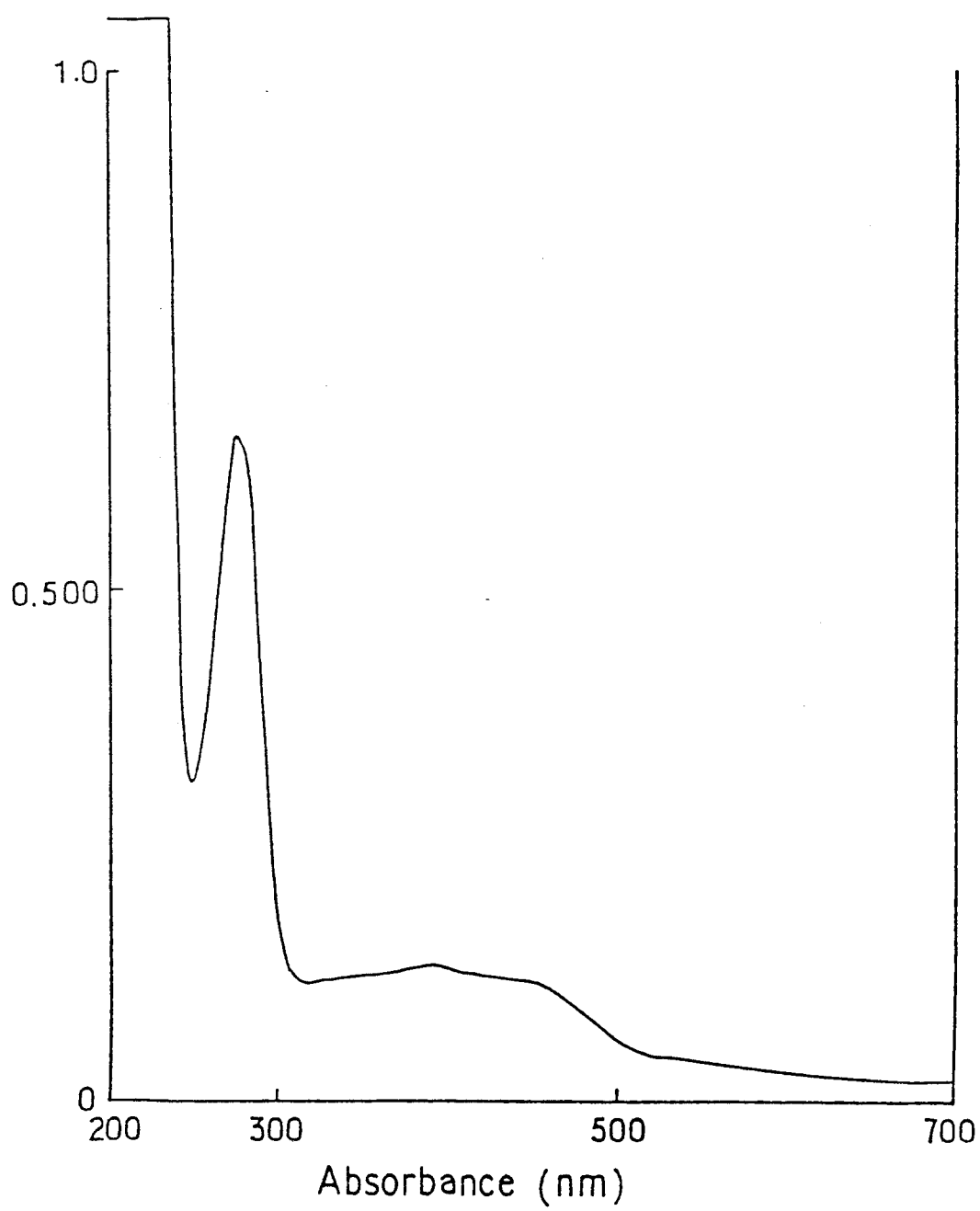
FIG. 6 is a diagram showing the result of spectral analysis of the present enzyme conducted in 100 mM phosphate buffer (pH 6.0)

The present enzyme was subjected to spectral analysis in 100 mM phosphate buffer (pH 6.0).
FIG. 6 shows the result.

(10) Metal Content

Atomic absorption spectrophotometry revealed that the enzyme contained iron, whereas none of molybdenum, copper, manganese and zinc were detected.

(11) Influence of Metal Ions on the Activity

A solution of the enzyme (0.02 U) was caused to act on inosine at pH 6.0 and 25° C. for 10 minutes in the presence of various metal ions, and the activity of the enzyme was thereafter measured to check the influence of the metal ions on the activity.
Table 7 shows the result.

TABLE 7

| Metal salt used | Concentration (mM) | Relative activity (%) |
|---|---|---|
| None | — | 100 |
| $MgSO_4$ | 0.1 | 102 |
| $ZnSO_4$ | 0.1 | 106 |
| $ZnSO_4$ | 1.0 | 98.9 |
| $MnSO_4$ | 0.1 | 103 |
| $CuSO_4$ | 0.1 | 108 |
| $CuSO_4$ | 1.0 | 102 |
| $FeSO_4$ | 0.1 | 93.4 |
| $CoCl_2$ | 0.1 | 103 |
| $(NH_4)_6Mo_7O_{24}$ | 0.1 | 106 |
| $(NH_4)_6Mo_7O_{24}$ | 1.0 | 102 |

(12) Km Value

The apparent Km value for inosine was found to be $4.4 \times 10^{-5}$ M.

(13) Amino Acid Composition

The present enzyme was hydrolyzed in a vacuum with use of 6N hydrochloric acid for 24, 48 or 72 hours. After thoroughly removing the acid, the decomposition mixture was dissolved in 0.09M citrate buffer (pH 2.2), and the solution was used for amino acid analysis by using automatic amino acid analyzer, Model JLC200A, product of Nippon Denshi Co., Ltd.
For the quantitative determination of tryptophan (Trp), the enzyme was hydrolyzed with 4.2N NaOH at 110° C. for 24 hours and thereafter analyzed similarly. For cystine (Cys), the enzyme was oxidized with performic acid, then decomposed with hydrochloric acid and thereafter analyzed (S. Moore, J. Biol. Chem., 238, 235(1963)).
Table 8 below shows the result.

TABLE 8

| Amino acid | Number of residues | Amino acid | Number of residues |
|---|---|---|---|
| Asp | 121 | Ile | 50 |
| Thr | 88 | Leu | 81 |
| Ser | 80 | Tyr | 52 |
| Glu | 96 | Phe | 41 |
| Pro | 94 | His | 16 |
| Gly | 86 | Lys | 47 |
| Ala | 94 | Arg | 33 |
| Val | 67 | ½ Cys | 10 |
| Met | 16 | Trp | 19 |

(14) Disk Electrophoresis

The present enzyme was subjected to disk electrophoresis in two lanes according to the method of Davis (J. B. Davis, Ann. N.Y. Acad. Sci., 121, 404(1964)) using 7% polyacrylamide gel (pH 9.5). One lane was used for protein staining, the other was cut into 1-mm units and usd for the determination of activity to check the electrophoretic mobility.
Consequently, the enzyme migrated as a single band, and the electrophoretic mobility was found in concidence with that of the activity.
Examples are given below wherein the present enzyme was used for the assay method of the invention. The enzyme used in these examples is the purified smaple of nucleoside oxidase YT-1 obtained in Example 3.

EXAMPLE 4

| 4-Aminoantipyrine | 23.4 mg |
|---|---|
| 5% Phenol | 2 ml |
| 50 mM HEPES buffer (pH 7.5) | 98 ml |
| Total | 100 ml |

Figure 7:
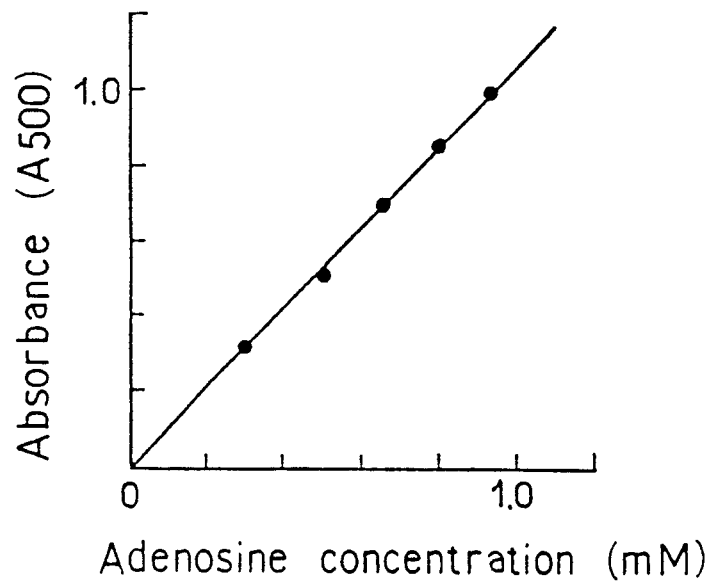
FIGS. 7 and 10 are graphs each showing the relationship between the amount of nucleoside in one of different test specimens and the absorbance measured, the illustrated results being obtained in Examples 4 and 5.

A 10 μl quantity of nucleoside oxidase (0.35 U) was added to 2.0 ml of chromogenic solution of the above composition. Subsequently, 0.3 ml of test sample containing a specified concentration of adenosine was added to the solution, the mixture was reacted at 30° C. for 20 minutes, and absorbance at 500 nm was then measured.
The result is given in FIG. 7, wherein the absorbance is plotted as ordinate vs. the adenosine concentration (mM) of the test sample as abscissa.
FIG. 7 shows that the adenosine in the test sample can be quantitatively determined easily and accurately by measuring the absorbance.

EXAMPLE 5

| 4-Aminoantipyrine | 23.4 mg |
|---|---|
| N-Ethyl-N-(2-hydroxy-3-sulfopropyl)-3,5-dimethylaniline | 178.7 mg |
| 50 mM phosphate buffer (pH 6.0) | 100 ml |
| Total | 100 ml |

A 10 μl quantity of nucleoside oxidase (0.35 U) was added to 2.0 ml of chromogenic solution of the above composition. Subsequently, 0.3 ml of test sample containing inosine, guanosine or deoxyadenosine at a specified concentration was added to the solution. The mixture was reacted at 30° C. for 20 minutes and then checked for absorbance at 630 nm.

Figure 8:
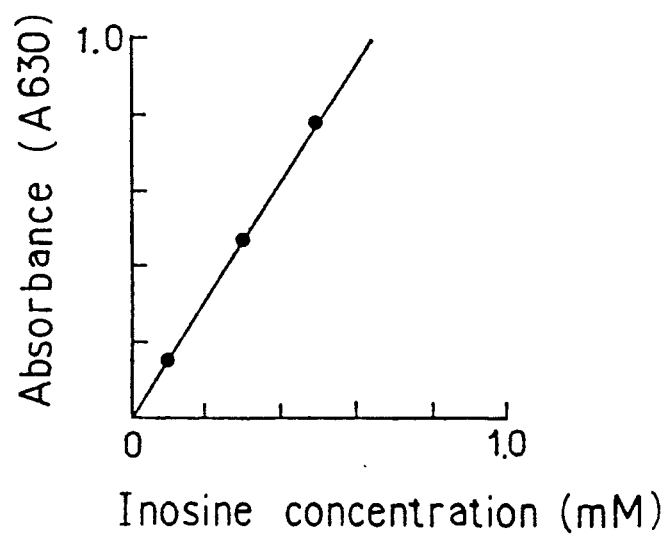
Figure 9:
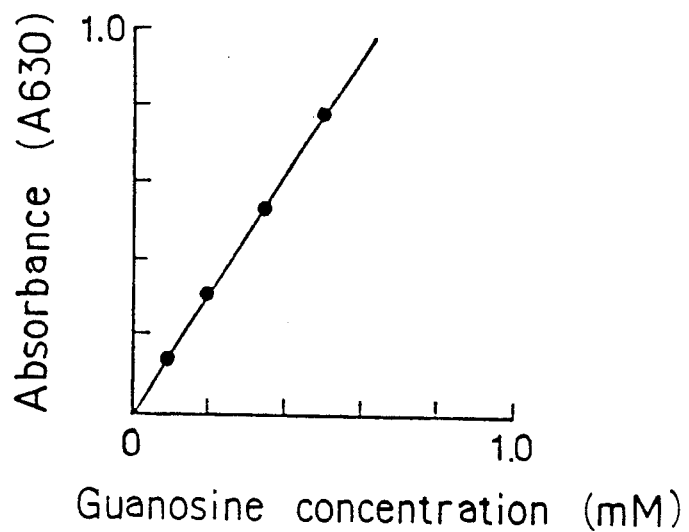
Figure 10:
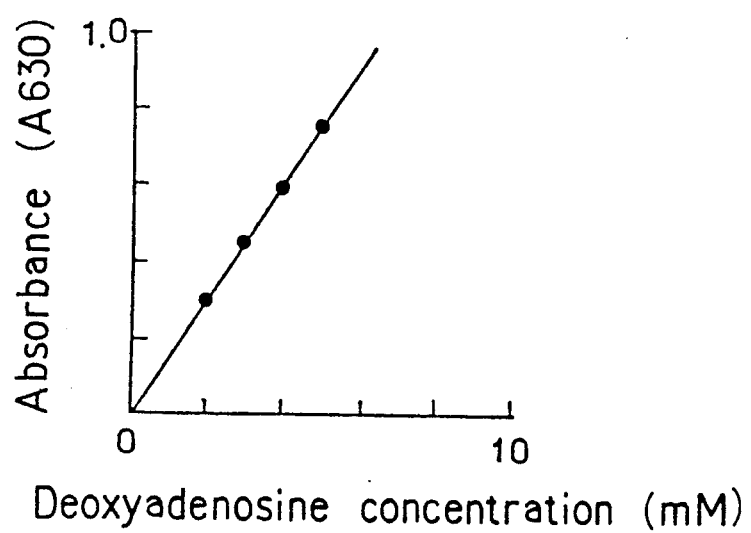

In the same manner as in FIG. 7, the result is shown in FIG. 8 (measurements for inosine), FIG. 9 (for guanosine) and FIG. 10 (for deoxyadenosine).

The diagrams indicate that the nucleosides in the test samples can be quantitatively determined easily and accurately by measuring the absorbance.

EXAMPLE 6

| 4-Aminoantipyrine | 23.4 mg |
|---|---|
| N-Ethyl-N-(2-hydroxy-3-sulfopropyl)-m-toluidine | 171.3 mg |
| Glycerol-2-phosphoric acid.2Na | 1.76 g |
| $MnSO_4.4-6H_2O$ | 19.4 mg |
| 50 mM HEPES buffer (pH 7.5) | 100 ml |
| Total | 100 ml |

A 10 μl quantity of nucleoside oxidase (0.35 U) was added to 2.0 ml of chromogenic solution of the above composition. Subsequently, 0.1 ml of test sample containing 5'-nucleotidase (product of Sigma, 5'-ND control E) at a specified concentration was added to the solution, 0.2 ml of 11.5 mM 5'-adenylic acid (5'-AMP) solution as a substrate was further added, and the mixture was checked for the increase in the absorbance at 555 nm per unit time for about 5 minutes using a spectrophotometer.

Figure 11:
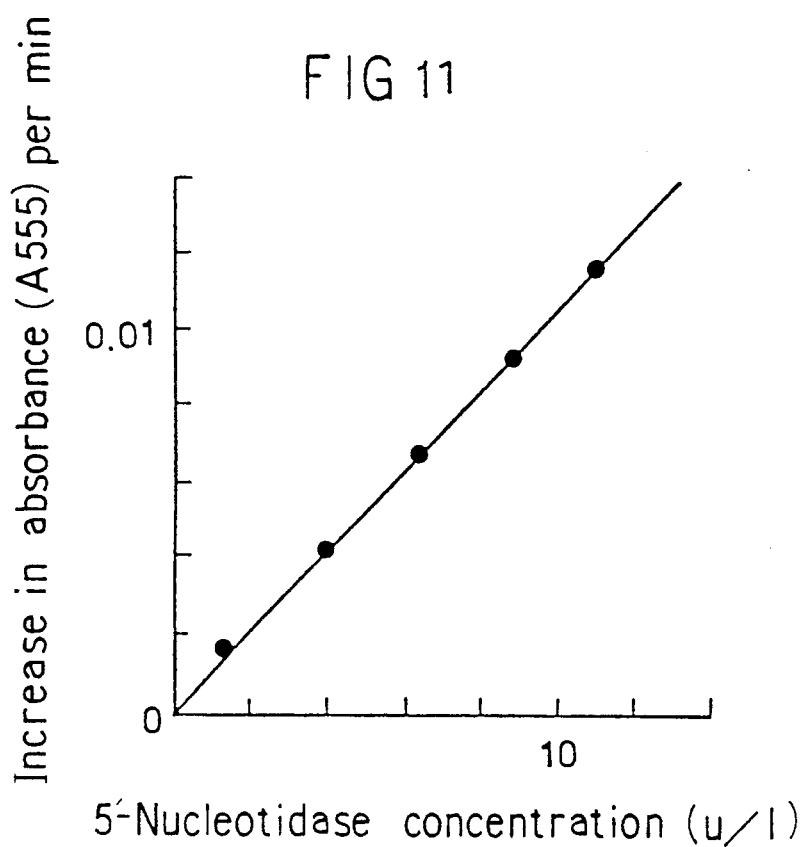
FIGS. 11 and 12 are graphs showing the relationship between the amount of nucleoside in a specimen and the absorbance measured, as determined in Examples 6 and 7.

The result is given in FIG. 11, in which the increase in absorbance per minute is plotted as ordinate, and concentration of 5'-nucleotidase (U/liter) as abscissa.

FIG. 11 shows that the nucleotidase in the test sample can be quantitatively determined easily and accurately by measuring the absorbance.

EXAMPLE 7

| 4-Aminoantipyrine | 23.4 mg |
|---|---|
| 5% Phenol | 2 ml |
| $MnSO_4.4-6H_2O$ | 19.4 mg |
| 50 mM HEPES buffer (pH 7.5) | 98 ml |
| Total | 100 ml |

A 10 μl quantity of nucleoside oxidase (0.35 U) was aded to 2.0 ml of chromogenic solution of the above composition. Subsequently, 0.1 ml of test sample containing 3'-nucleotidase (product of Sigma) at a specified concentration was added to the solution, followed by the addition of the solution of 0.2 ml of 11.5 mM 3'-adenylic acid (3'-AMP) as a substrate. The mixture was checked for the increase in the absorbance at 505 nm per unit time for abut 5 minutes using a spectrophotometer.

Figure 12:
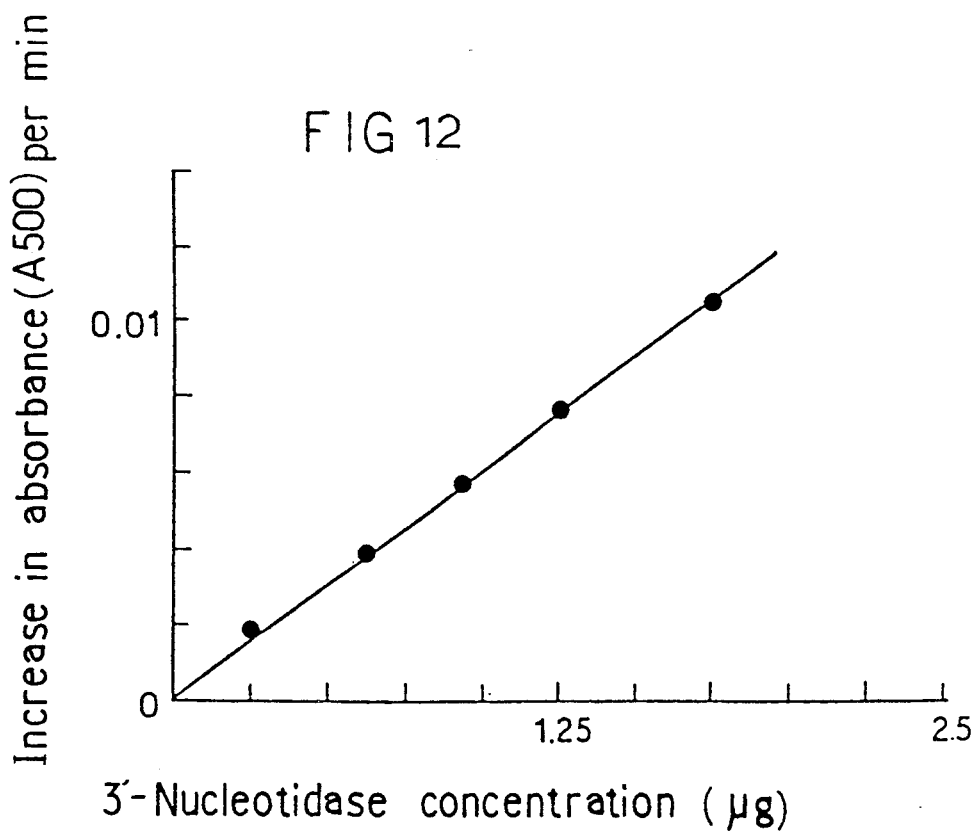

In the same manner as in FIG. 11, the result is shown in FIG. 12.

The diagram reveals that the nucleotidase in the test sample can be quantitatively determined easily, promptly and accurately.

EXAMPLE 8

To the same chromogenic solution as used in Example 6 were added 10 μl (0.35 U) of nucleoside oxidase and 0.1 ml of human serum. Subsequently, 0.2 ml of 5'-AMP(11.5 AMP (11.5 mM) was added to the mixture, and the increase in absorbance at 555 nm was measured by a spectrophotometer to determine the activity of 5'-nucleotidase in the human serum.

Table 9 below shows the result obtained by repeating the above procedure 15 times using the same serum sample.

TABLE 9

| Number of repetitions | 15 |
|---|---|
| Mean measurement | 7.1 U/liter |
| Standard deviation | 0.1 U/liter |
| Coefficient of variation | 1.4% |

The above table reveals that the 5'-nucleotidase activity in the human serum can be measured by the present assay method with high reproducibility.

EXAMPLE 9

In the same manner as in Example 8, the activity of 5'-nucleotidase was assayed for 18 human serum samples.

For comparison, the known enzymatic method (C. L. M. Arkesteijn, J. Clin. Chem. Clin. Biochem., Vol. 14, PP. 155-158(1976)) was practiced for the same human serum samples to determine the same enzymatic activity.

Figure 13:
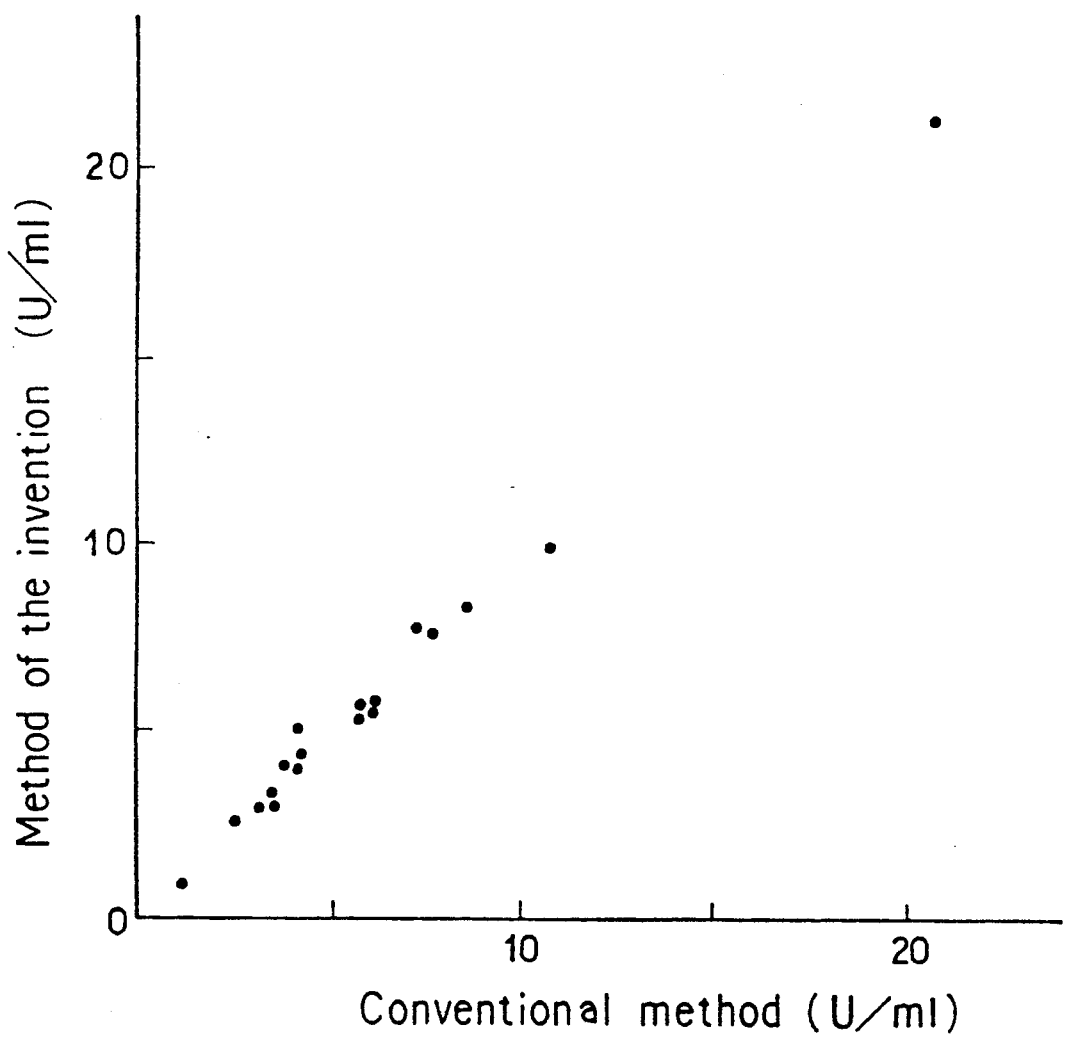
FIG. 13 is a graph showing the result obtained by measuring the activity of 5'-nucleotidase in human serum according to Example 9.

FIG. 13 shows the results obtained.

In FIG. 13, the result (U/ml) achieved by the conventional method is plotted as abscissa vs. the result (U/ml) by the method of the invention as ordinate, the diagram thus showing all the results achieved for the samples by the two methods. The correlation coefficient calculated from the diagram was 0.994, indicating a very high correlation between the two assay methods.

The foregoing results demonstrate that the present assay method is usable for determining the activity of 5'-nucleotidase in the human serum with high sensitivity promptly through a greatly simplified procedure in place of the conventional method which has the drawbacks of necessitating a complex assay system and a preliminary reaction for about 30 minutes prior to the start of the main reaction.

EXAMPLE 10

A 1 ml quantity of 1 mM o-toluidine solution was added to 2 ml of 100 mM phosphate buffer (pH 6.0) containing inosine at a speicified concentration, 10 μl of nucleoside oxidase (0.35 U) was further added, and the mixture was reacted at 37° C. for 15 minutes and thereafter checked for absorbance at 480 nm.

Figure 14:
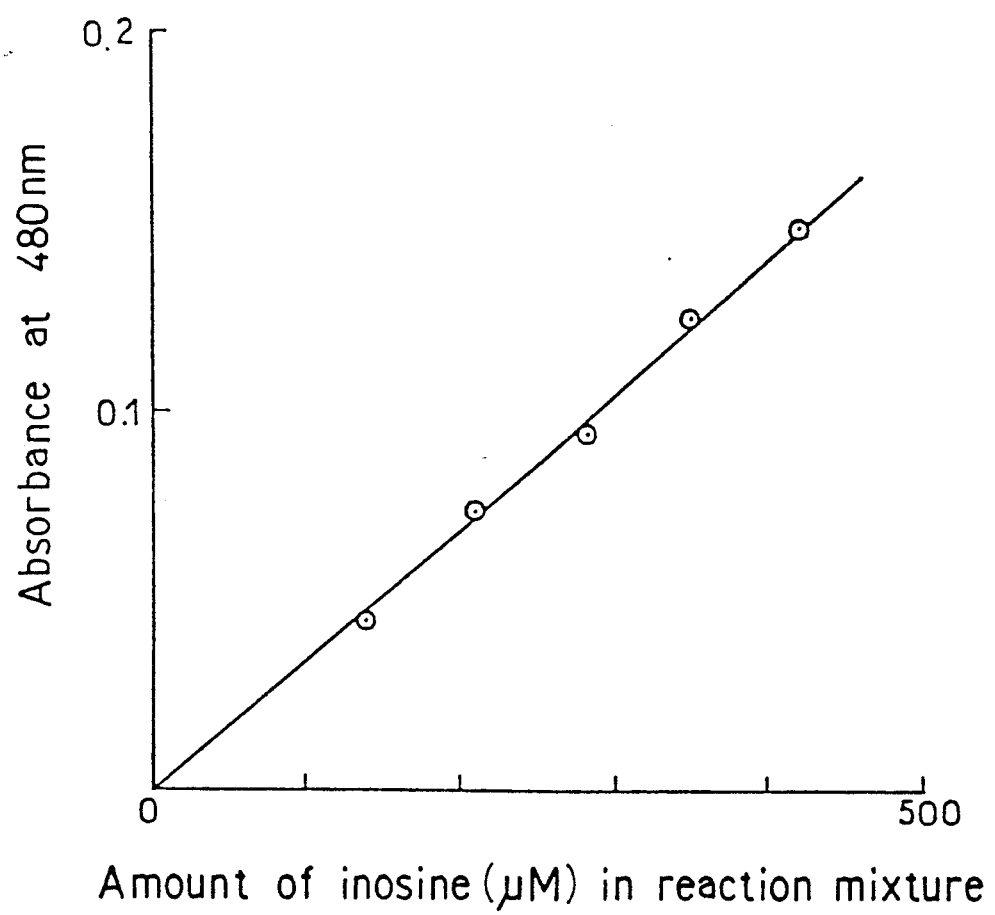
FIG. 14 is a graph showing the result of measurement (relationship between the amount of inosine and the absorbance measured) according to Example 10.

The result is shown in FIG. 14, in which the absorbance at 480 nm is plotted as ordinate, and the amount of inosine (μM) in the reaction mixture as abscissa.

The diagram indicates that the amount of inosine in the samples can be measured accurately utilizing the proportional relationship between the inosine content of the samples and the absorbance thereof.

*Pseudomonas maltophilia* LB-86 for use in the present invention has been deposited with the above designation and deposition number FERM P-9813 in the Fermentation Research Institute, Agency of Industrial Science and Technology, MITI 1-3, Higashi 1-chome Tsukuba-shi, Ibaraki-ken 305, Japan, since Jan. 14, 1988, with the deposition number changed to FERM BP-2252 on Jan. 20, 1989.

We claim:

1. An isolated and purified nucleoside oxidase YT-1 which is an enzyme for catalyzing an oxidation reaction of a nucleoside, wherein the oxidase causes the nucleoside to react with molecular oxygen to produce a nucleoside-5'-carboxylic acid via a nucleoside-5'aldehyde without producing hydrogen peroxide.

2. A process for producing a nucleoside oxidase YT-1 comprising:
  (1) incubating on a nutrient medium a microorganism which is a *Pseudomonas maltophilia LB*-86 and which is able to produce said nucleoside oxidase YT-1 which is an enzyme for catalyzing an oxidation reaction of a nucleoside, wherein the oxidase causes the nucleoside to react with molecular oxygen to produce a nucleoside-5'-carboxylic acid via a nucleoside-5'-aldehyde without producing hydrogen peroxide, and
  (2) collecting the oxidase YT-1 from the resulting culture.

3. A biologically pure culture of a microorganism, wherein the microorganism is a *Pseudomonas maltophilia* LB-86 and is able to produce a nucleoside oxidase YT-1 which is an enzyme for catalyzing an oxidation reaction of a nucleoside, wherein the oxidase causes the nucleoside to react with molecular oxygen to produce a nucleoside-5'-carboxylic acid via a nucleoside-5'-aldehyde without producing hydrogen peroxide.

4. A microorganism as defined in claim 3, wherein the microorganism is FERM BP-2252.

5. A method of assaying a sample for the presence of a nucleoside, comprising
  (1) reacting:
    (a) a nucleoside oxidase YT-1 which is an enzyme for catalyzing an oxidation reaction of a nucleoside, wherein the oxidase causes the nucleoside to react with molecular oxygen to produce a nucleoside-5'-carboxylic acid via a nucleoside-5'-aldehyde without producing hydrogen peroxide, with
    (b) a mixture of the sample and a chromogenic reagent forming a color on oxidation, and
  (2) measuring the degree of color formation by the chromogenic reagent which is proportional to the variation in the quantity of nucleoside in the sample.

6. An assay method as defined in claim 5, wherein the sample is selected from among a sample containing the nucleoside, an enzymatic reaction system for releasing the nucleoside and an enzymatic reaction system for decomposing the nucleoside.

7. An assay method as defined in claim 5, wherein the sample is a nucleoside releasing enzymatic reaction system containing human serum and a nucleotide to determine the activity of 5'-nucleotidase in human serum.

* * * * *